US010814077B2

(12) United States Patent
Dyche et al.

(10) Patent No.: US 10,814,077 B2
(45) Date of Patent: Oct. 27, 2020

(54) CARTRIDGE FOR SUBSTANCE DELIVERY MODULE

(71) Applicant: KONINKLIJKE PHILIPS N.V., Eindhoven (NL)

(72) Inventors: Anthony Dyche, Hampshire (GB); Ian Thomas Petherbridge, West Sussex (GB)

(73) Assignee: Koninklijke Philips N.V., Eindhoven (NL)

( * ) Notice: Subject to any disclaimer, the term of this patent is extended or adjusted under 35 U.S.C. 154(b) by 1039 days.

(21) Appl. No.: 14/890,732

(22) PCT Filed: May 9, 2014

(86) PCT No.: PCT/EP2014/059507
§ 371 (c)(1),
(2) Date: Nov. 12, 2015

(87) PCT Pub. No.: WO2014/184095
PCT Pub. Date: Nov. 20, 2014

(65) Prior Publication Data
US 2016/0089507 A1 Mar. 31, 2016

(30) Foreign Application Priority Data

May 17, 2013 (EP) ..................................... 13168179

(51) Int. Cl.
*A61M 15/00* (2006.01)
*A61M 11/00* (2006.01)
*A61M 16/00* (2006.01)

(52) U.S. Cl.
CPC ........ *A61M 15/005* (2014.02); *A61M 11/005* (2013.01); *A61M 11/007* (2014.02);
(Continued)

(58) Field of Classification Search
CPC ............ A61M 15/005; A61M 15/0041; A61M 15/0038; A61M 15/007; A61M 15/004;
(Continued)

(56) References Cited

U.S. PATENT DOCUMENTS

| 5,584,417 A | 12/1996 | Graf |
| 5,881,719 A * | 3/1999 | Gottenauer ....... A61M 15/0045 128/203.15 |

(Continued)

FOREIGN PATENT DOCUMENTS

| DE | 202012104328 U1 | 11/2012 |
| EP | 2082769 A1 | 7/2009 |
| JP | H05507671 A | 11/1993 |

*Primary Examiner* — Colin W Stuart
*Assistant Examiner* — Douglas Y Sul
(74) *Attorney, Agent, or Firm* — Daniel H. Brean

(57) ABSTRACT

A substance delivery module and apparatus for delivering substance in aerosol form are disclosed. The substance delivery module includes a plurality of substance containers and a plurality of pistons, with each substance container being mounted in the module for cooperation with a dedicated piston. Another substance delivery module is disclosed that includes a piston defining a delivery axis and a substance container, moveably mounted with respect to the piston. The substance container is moveable along the delivery axis and may, for example, be moved toward and onto the piston. Either of the substance delivery modules may be assembled with an aerosol generator and an aerosol delivery conduit in fluid communication with the aerosol generator to form an apparatus for delivering substance in aerosol form. The apparatus may further include a control module.

**

(52) U.S. Cl.
CPC ...... *A61M 15/004* (2014.02); *A61M 15/0021* (2014.02); *A61M 15/0036* (2014.02); *A61M 15/0038* (2014.02); *A61M 15/0041* (2014.02); *A61M 15/0048* (2014.02); *A61M 15/0085* (2013.01); *A61M 15/002* (2014.02); *A61M 15/0003* (2014.02); *A61M 15/0015* (2014.02); *A61M 2016/0021* (2013.01); *A61M 2016/0027* (2013.01); *A61M 2205/0205* (2013.01); *A61M 2205/0238* (2013.01); *A61M 2205/123* (2013.01); *A61M 2205/6054* (2013.01); *A61M 2205/8206* (2013.01)

(58) Field of Classification Search
CPC .......... A61M 15/0003; A61M 15/0028; A61M 15/0035; A61M 2205/0205
See application file for complete search history.

(56) References Cited

U.S. PATENT DOCUMENTS

| | | |
|---|---|---|
| 7,219,665 B1 * | 5/2007 | Braithwaite ...... A61M 15/0045 128/203.12 |
| 2003/0163099 A1 | 8/2003 | Wermeling |
| 2004/0188546 A1 * | 9/2004 | Tabata ................ A61M 15/0085 239/436 |
| 2006/0107957 A1 * | 5/2006 | Djupesland ........... A61M 15/08 128/206.11 |
| 2007/0151562 A1 | 7/2007 | Jones |
| 2008/0142008 A1 | 6/2008 | Pocock |
| 2008/0177246 A1 | 7/2008 | Sullivan |
| 2008/0210229 A1 | 9/2008 | Corbacho |
| 2009/0013994 A1 * | 1/2009 | Jones ................ A61M 15/0088 128/200.23 |
| 2009/0223515 A1 | 9/2009 | Watanabe |
| 2009/0236374 A1 * | 9/2009 | Pardes ................ A61F 9/0008 222/494 |
| 2010/0095957 A1 | 4/2010 | Corbacho |
| 2010/0258121 A1 | 10/2010 | Kirniak |
| 2010/0319693 A1 | 12/2010 | Fagot |
| 2010/0331765 A1 | 12/2010 | Sullivan |
| 2013/0032144 A1 | 2/2013 | Miller |
| 2016/0121057 A1 * | 5/2016 | Dyche ................ A61M 15/009 128/200.23 |

* cited by examiner

CARTRIDGE FOR SUBSTANCE DELIVERY MODULE

CROSS-REFERENCE TO RELATED APPLICATIONS

This patent application claims the priority benefit under 35 U.S.C. § 371 of international patent application no. PCT/EP2014/059507, filed May 9, 2014, which claims the benefit of European Patent Application No. 13168179.3, filed on May 17, 2013. These applications are hereby incorporated by reference herein.

TECHNICAL FIELD

The present invention relates to a substance delivery module, and particularly but not exclusively to a substance delivery module for use in an apparatus for delivering a substance in aerosol form.

BACKGROUND

Medicinal substances such as drugs and other medications are often required to be delivered in aerosol form for inhalation into the lungs of a patient. Various devices are available for delivery of medicinal substances in aerosol form, including for example nebulizers. A nebulizer is a device designed to convert a liquid substance into an aerosol which may then be inhaled by a patient, typically via a mouthpiece. Different types of nebulizer exist, using different technologies to convert the liquid substance to aerosol form. Two of the more popular technologies are jet nebulizers, which introduce compressed air to the liquid substance, and vibrating mesh nebulizers, which use a fine mesh vibrating at ultrasonic frequencies to generate a mist of substance droplets.

Medicinal substances are typically required to be delivered as controlled doses of a specific volume, and dose control is one area of nebulizer technology which has received attention. In order to provide greater control over the volume of substance delivered with each use of the nebulizer, some nebulizers have incorporated a multi dose system, in which individual doses of liquid substance are provided in place of a single liquid reservoir. An example of such a system is disclosed in US 2003/0163099, in which a plurality of sealed vials of medicinal liquid are mounted on a support member for sequential dispensing via a plunger. While such multi dose systems provide improvements in dose control over single reservoir systems, difficulties remain in assuring ease of use and in accommodating the requirements of differing regimes for the dispensing of medicinal substances.

SUMMARY

Aspects of the present invention seek to provide a module and apparatus which obviate or reduce at least one of the disadvantages mentioned above.

According to a first aspect of the present invention, there is provided a substance delivery module comprising a plurality of substance containers and a plurality of pistons, wherein each substance container is mounted in the module for cooperation with a dedicated piston.

The substance containers may be suitable for containing a liquid substance including for example a medicinal liquid substance such as a drug in liquid form. According to some embodiments, one or more substance containers may contain a substance that is different to that contained in one or more other substance containers of the module. The different substances may for example be different medicinal substances.

According to some embodiments, the substance containers may be moveably mounted within the module, each substance container being mounted for motion onto its dedicated piston.

According to some embodiments, the pistons may be dimensioned to displace an internal volume of their respective substance containers, and may thus ensure that a maximum amount of substance held within the containers is displaced for example via a through passage of the piston. An outer diameter of a piston may sealingly engage an inner diameter of its respective container.

According to some embodiments, each piston having a cooperating substance container may comprise a passage extending through the piston. The passage may for example comprise a delivery conduit through which substance in the substance container may be delivered. The passage may extend from a leading to a trailing face of the piston.

According to some embodiments, the pistons may comprise individual cutting elements, each cutting element mounted on a leading surface of a piston. The cutting elements may for example be operable to pierce a substance container.

According to some embodiments, the cutting elements may be disposed about a leading opening of a through passage of a piston. The cutting elements may define cutting surfaces which are angled with respect to a delivery axis of the pistons.

According to some embodiments, the pistons may further comprise second individual cutting elements mounted about a rim of a leading surface of a piston.

According to some embodiments, each substance container may comprise a cup and sealing membrane and may be mounted in the module with the sealing membrane presented to a leading face of its dedicated piston.

According to some embodiments, the module may further comprise an actuator which may be configured to force relative motion between a substance container and its dedicated piston.

According to some embodiments, the actuator may be configured to engage a substance container and to urge the substance container onto its dedicated piston.

According to some embodiments, the actuator may be mounted for relative motion with respect to the substance containers. The actuator may be mounted for relative rotational motion with respect to the substance containers. According to other embodiments, the actuator may be mounted for relative translation with respect to the substance containers.

According to some embodiments, the module may comprise a plurality of actuators, each actuator being mounted for cooperation with a dedicated substance container.

According to some embodiments, the module may further comprise a cartridge, and the pistons and substance containers may be mounted within the cartridge.

According to another aspect of the present invention, there is provided a substance delivery module comprising a piston defining a delivery axis and a substance container moveably mounted with respect to the piston, wherein the substance container is moveable along the delivery axis.

According to some embodiments, the module may further comprise an actuator configured to engage the substance container and urge the substance container along the delivery axis. The actuator may be configured to urge the substance container onto the piston.

According to some embodiments, the piston may be dimensioned to displace an internal volume of the substance container, and may thus ensure that a maximum amount of substance held within the container is displaced for example via a through passage of the piston. An outer diameter of the piston may sealingly engage an inner diameter of the container.

According to some embodiments, the piston may comprise a passage extending therethrough. The passage may for example comprise a delivery conduit through which substance in the substance container may be delivered. The passage may extend from a leading to a trailing face of the piston along the delivery axis.

According to some embodiments, the piston may comprise a cutting element which may be mounted on a leading surface of the piston. The cutting element may for example be operable to pierce the substance container.

According to some embodiments, the cutting element may be disposed about a leading opening of a through passage of the piston. The cutting element may define a cutting surface which is angled with respect to the delivery axis of the piston.

According to some embodiments, the piston may further comprise a second cutting element mounted about a rim of the leading surface of the piston.

According to some embodiments, the substance container may comprise a cup and sealing membrane and may be mounted in the module with the sealing membrane presented to a leading face of the piston.

According to some embodiments, the module may comprise a plurality of pistons and a plurality of substance containers, each substance container moveably mounted for cooperation with a dedicated piston.

According to some embodiments, the module may further comprise a plurality of actuators, each actuator mounted for cooperation with a dedicated substance container.

According to another aspect of the present invention, there is provided an apparatus for delivering a substance in aerosol form, the apparatus comprising an aerosol generator, an aerosol delivery conduit in fluid communication with the aerosol generator, and a substance delivery module in accordance with the first or second aspects of the present invention.

According to some embodiments, at least part of the apparatus may comprise an anti-microbial surface. The anti-microbial surface may be formed by coating or creating a part of the apparatus from/with an anti-microbial material (for example silver) or by treating a part of the apparatus with an antimicrobial process (for example ultra violet light).

These and other aspects of the invention will be apparent from and elucidated with reference to the embodiments described below.

BRIEF DESCRIPTION OF THE DRAWINGS

For a better understanding of the present invention, and to show more clearly how it may be carried into effect, reference will now be made, by way of example only, to the following drawings in which.

DETAILED DESCRIPTION

Embodiments of the present invention provide a substance delivery module and substance delivery apparatus that enable controlled delivery of a dose of substance contained within the apparatus or module. The apparatus and module may be used for example to deliver liquid medicinal substances in aerosol form.

Figure 1:
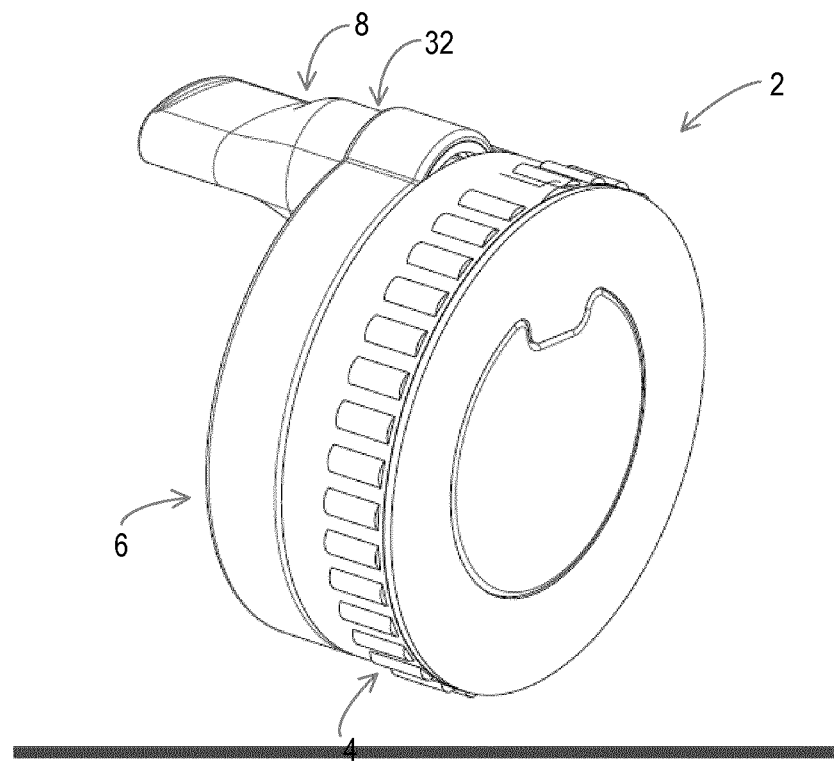
FIG. 1 is a perspective view of a nebulizer.

Referring to FIG. 1, an embodiment of an apparatus for delivering a substance in aerosol form may take the form of a nebulizer 2. The nebulizer 2 comprises a substance delivery module 4, a control module 6 and a mouthpiece 8.

Figure 2:
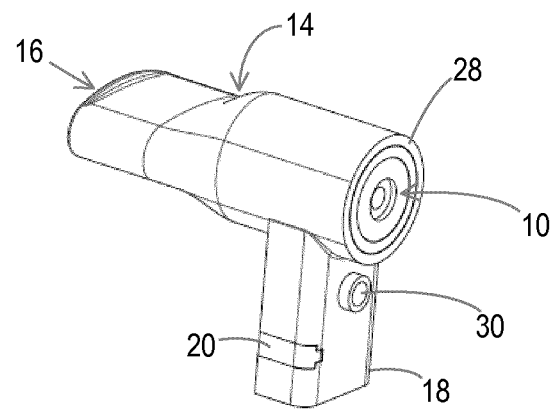
FIG. 2 is a perspective view of a mouthpiece of the nebulizer of FIG. 1.
Figure 3:
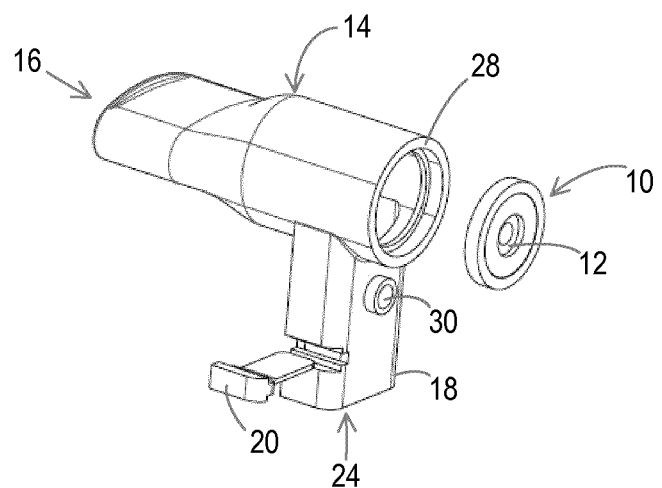
FIG. 3 is an exploded view of the mouthpiece of FIG. 2.
Figure 4:
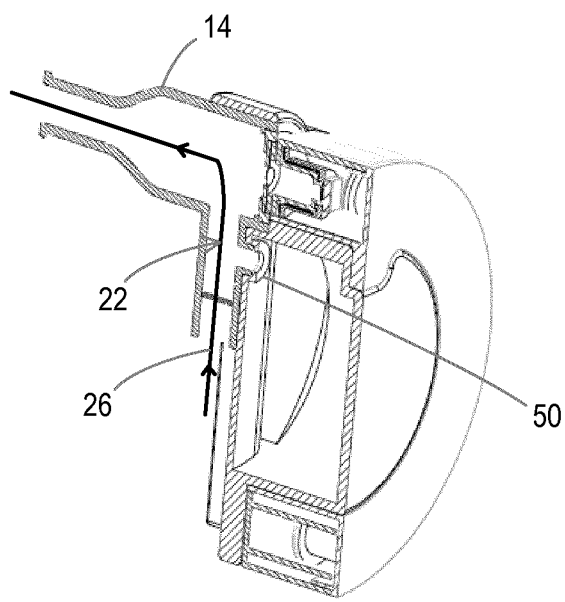
FIG. 4 is a sectioned perspective view of the nebulizer of FIG. 1.

Referring also to FIGS. 2, 3 and 4, the nebulizer further comprises an aerosol generator 10 in the form of a piezo electric mesh 12 mounted within a housing 28 in the mouthpiece 8. The mouthpiece 8 comprises an aerosol delivery conduit 14 leading from the aerosol generator 10 to an opening 16 sized to be placed in the mouth of a patient for inhalation of a substance dispensed in aerosol form by the nebulizer 2. The mouthpiece 8 further comprises an inhalation stem 18 within which is mounted a flow control valve 20. The inhalation stem comprises a through passage 22 that extends from an opening 24 via the flow control valve 20 to open into the aerosol delivery conduit 14. The inhalation stem and aerosol delivery conduit thus together define an inhalation flow path 26, as illustrated in FIG. 4. The inhalation stem further comprises an opening 30 extending through a wall of the stem to communicate with the inhalation flow path 26.

The housing 28 of the mouthpiece 8 is received within a recess 32 formed in the control module 6, such that the aerosol generator 10 is presented to, and in fluid communication with, the output of a substance feed system formed in the substance delivery module 4, as explained in further detail below.

The control module 6 comprises a substantially sealed unit within which is housed power and control circuitry. The power and control circuitry may include a battery or other power source, an electronic tagging device such as an RFID tag, a memory and circuitry to power a patient display panel such as a screen, LED indicator light etc. The control module may further comprise one or more activation elements which may take the form of a solenoid switch or switches. The activation elements may form part of an indexing mechanism and in some embodiments may activate delivery of substance contained in the substance delivery module, as discussed in further detail below. The control module also houses the drive circuitry for the aerosol generator 10. The electrical connection between the aerosol generator 10 and the control module 6 may use physical contacts or inductive coupling.

The functioning of the control module is discussed in detail below with respect to the operation different embodiments of the nebulizer 2. The configuration of the control module 6 may be adapted according to the way in which delivery of substance is activated. Example configurations of control modules are discussed with reference to particular embodiments.

Figure 5:
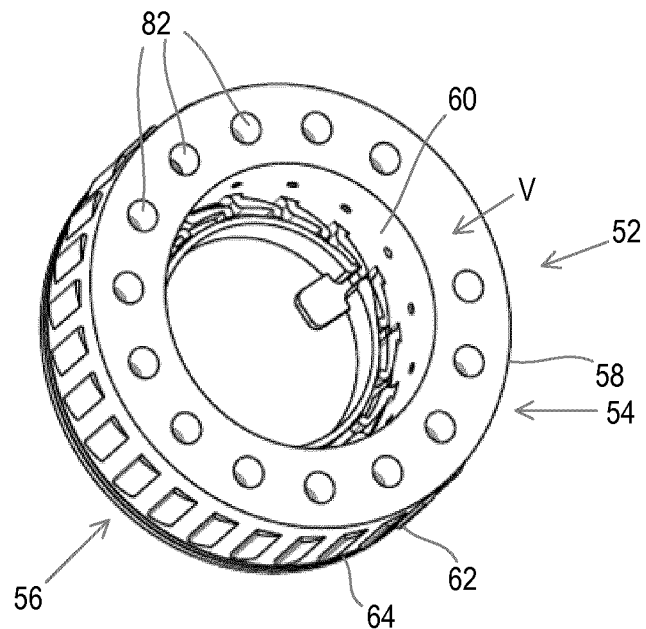
FIG. 5 is a perspective view of a substance delivery module.
Figure 6:
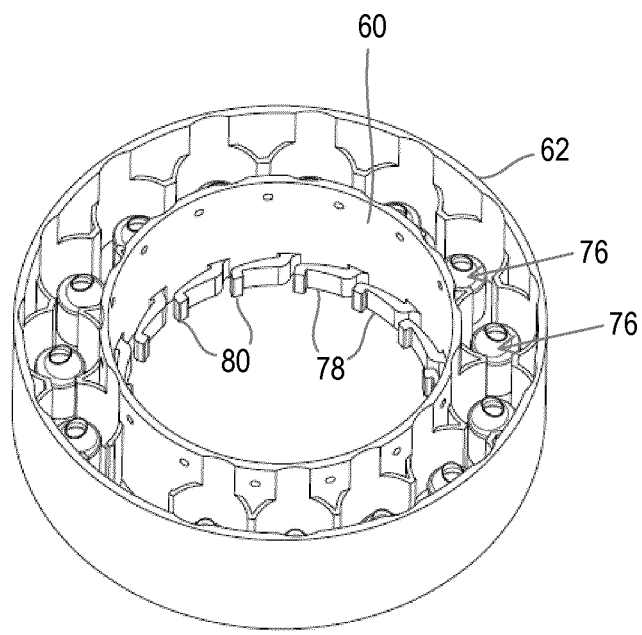
FIG. 6 is a perspective view of a cartridge base.
Figure 7:
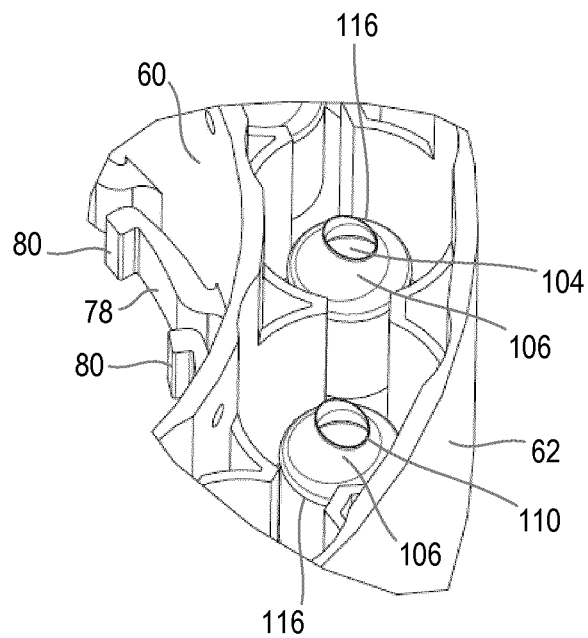
FIG. 7 is a detail view of a part of the cartridge base of FIG. 6.

Referring to FIGS. 5 to 7, the substance delivery module 4 comprises a cartridge 52 having a cartridge base 54 and cartridge lid 56. The cartridge base 54 comprises an annular structure having a base plate 58, inner annular wall 60, and outer annular wall 62. The outer annular wall 62 may comprise a plurality of gripping protrusions 64 formed on an outer surface thereof. The cartridge lid 56 comprises an annular top plate 66 and may comprise an inner and/or outer annular skirt.

The substance delivery module 4 further comprises a plurality of delivery pistons 76 mounted in the cartridge base 54. In an alternative embodiment (not shown), only a single piston 76 may be mounted in the cartridge base 52. In the illustrated embodiment the pistons 76 are integrally formed with the cartridge but in alternative embodiments, the pistons may be separately formed and fixed in place in the cartridge base 54. The or each piston 76 defines a longitudinal delivery axis 150, along which medicinal substance is dispensed.

Protruding from the inner annular wall of the cartridge base 54 is a plurality of indexing arms 78, substantially evenly distributed around the inner circumference of the wall 60. Each arm 78 terminates in a locking rib 80. Each of the locking ribs 80 is dimensioned to be received in an opening as part of an indexing system for the cartridge. The indexing arms 78 are resilient, able to support mild deflection such that the locking rib 80 on the end of each arm may be disengaged from an opening while the remainder of the cartridge base 54 remains in place. As illustrated most clearly in FIG. 5, the base plate 58 of the cartridge base 54 comprises a plurality of openings 82, each of which corresponds to a through passage formed through a delivery piston 76 as described below.

As discussed above, a plurality of pistons 76 are mounted within the cartridge base 54. Axially aligned with each piston 76 is a substance container or vial 90. Together, each pair of delivery piston 76 and aligned vial 90 forms a dedicated feed system for the substance contained in the vial 90. In the illustrated embodiment the cartridge 52 is loaded with 14 vials 90, each having a dedicated delivery piston 76. The 14 vials represent for example a one week course of drugs comprising a twice daily dose. A fifteenth position V on the cartridge 52 may be vacant, and may serve as an initial assembly position.

Figure 8A:
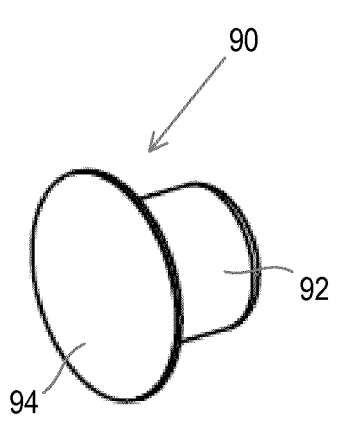
FIG. 8a is a perspective view of a substance container.
Figure 8B:
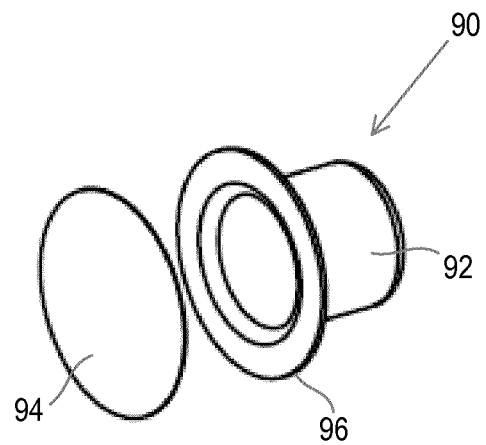
FIG. 8b is an exploded view of a substance container.

Referring now to FIGS. 8a and 8b, each vial 90 comprises a cup 92 and a sealing membrane 94. The cup comprises an annular lip 96 to which the membrane 94 is sealed. The substance to be dispensed is sealed within the cup by the membrane. Each vial 90 is mounted in the cartridge base 54 axially aligned with a piston 76, with the membrane 94 presented to the leading face of the piston 76. A single vial and corresponding piston can be seen in enlarged view in FIG. 9. It will be appreciated that each of the vials and pistons comprises corresponding features. The piston 76 comprises a through passage 102 extending along the delivery axis 150 from a leading opening 104 on a leading face 106 of the piston 62 to a delivery opening 108 which is coincident with the corresponding opening 82 formed in the base plate 58 of the cartridge base 54. The leading opening 104 is surrounded by a first cutting element 110 which extends towards the membrane 94 of the vial 90 and defines an angled cutting plane 112.

Figure 9:
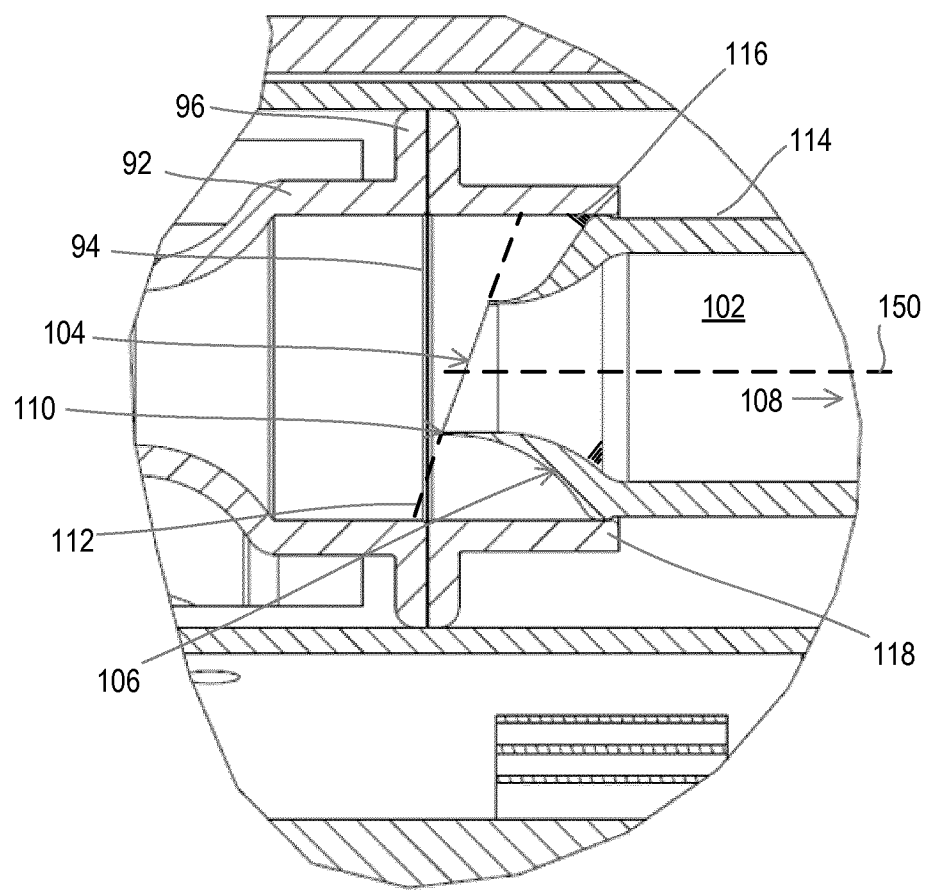
FIG. 9 is a partial sectional view of a substance container and piston.

A sealing sleeve 118 may surround the first cutting element 110 providing sliding sealing engagement between the vial 90 and an outer surface 114 of the piston 76. The sealing sleeve 118 may also act to guide the vial 90 onto the piston 76, as discussed below. In some embodiments, the sealing sleeve 118 may be formed integrally with the vial 90. In some embodiments, as illustrated in FIG. 9, the piston 76 may further comprise a second cutting element 116. The second cutting element 116 also extends towards the membrane 94 of the vial 90 and is mounted about a rim of the leading surface 106 of the piston 76.

One or more actuators may be mounted in the cartridge 52 to engage the vials 90 and urge the vials 90 onto their cooperating piston 76. During operation, and under the action of the or each actuator, a vial 90 is forced along the delivery axis 150 towards and onto the corresponding piston 76. The initial movement of the vial 90 onto the piston 76 causes the first cutting element 110 to pierce the membrane 94 allowing liquid from the vial 90 to start to enter the delivery passage 102 of the piston 76. The delivery passage 102 may have an internal diameter shaped to create a pressure gradient that encourages flow of the liquid in the vial into the passage 102. Continued pressure from the actuator forces the vial 90 further onto the piston 76, guided by the sleeve 118. As the vial 90 advances, the second cutting element 116 engages the membrane and completely separates the membrane 94 from the cup 92, allowing the membrane 94 to remain on the leading face 106 of the piston 76 as the piston progressively occupies the internal volume of the cup 92. By separating the membrane 94 from the cup 92 in this manner, the membrane is prevented from interfering with the seal between an outer diameter of the piston and inner diameter of the cup 92, so minimising leakage between the piston 76 and vial 90. The actuator forces the vial 90 completely over the piston 76, until the full internal volume of the vial is occupied, and all liquid contained in the vial has been displaced.

The external surface of the piston is shaped substantially to displace the entire internal volume of the vial 90, so ensuring that a maximum amount of liquid is emptied from the vial and delivered to the through passage of the piston 76. The through passage 102 delivers the liquid from the vial 90 to the delivery opening 108. When the substance delivery module 4 is assembled with the control module 6 and mouthpiece 8, the delivery opening 108 delivers the substance via an opening in the control module directly to the aerosol generator 10. The aerosol generator 10 may thus aerosolise the liquid substance and deliver the substance in aerosol form into the inhalation flow path 26 to be entrained with inhaled air and drawn into the lungs of the patient. The piston 76 and vial 90 thus cooperate under the action of an actuator to deliver a maximum amount of a dose of liquid substance to the aerosol generator 10. A vent (not shown) may be mounted on adjacent each piston 76 and between the piston 76 and aerosol generator 10, to allow for escape of any air in the feed system during dispensing of the substance. The vent may prevent substance escape and may include a non return valve to prevent air entering the feed system between dispensing of vials. The vent may also allow air to replace liquid during aerosolization.

As discussed above, a single or multiple actuators may be employed to engage the vials 90 and so cause dispensing of the substance contained within the vials. Embodiments having a single and multiple actuators are discussed below. As illustrated in the following disclosure, the number and configuration of actuators may influence the configuration of the cartridge base 54 and lid 56, and of the control module 6.

Figure 10:
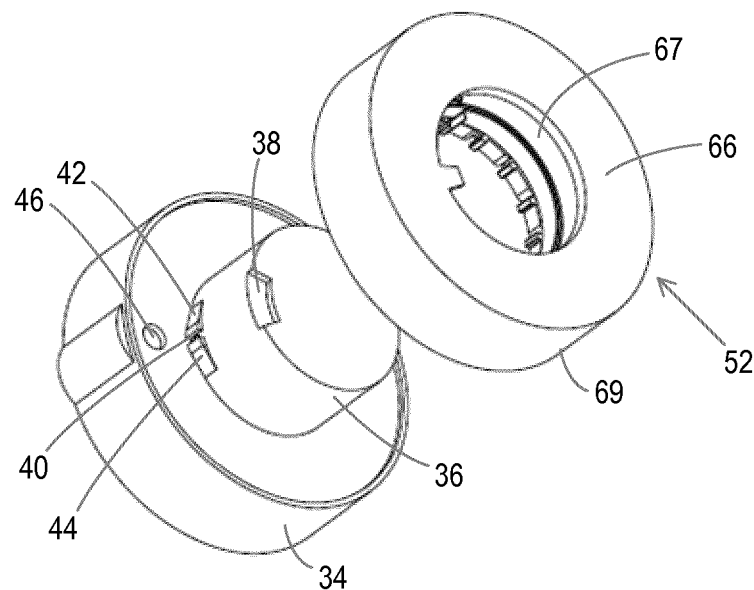
FIG. 10 is an exploded view of a control module and substance delivery module.
Figure 11:
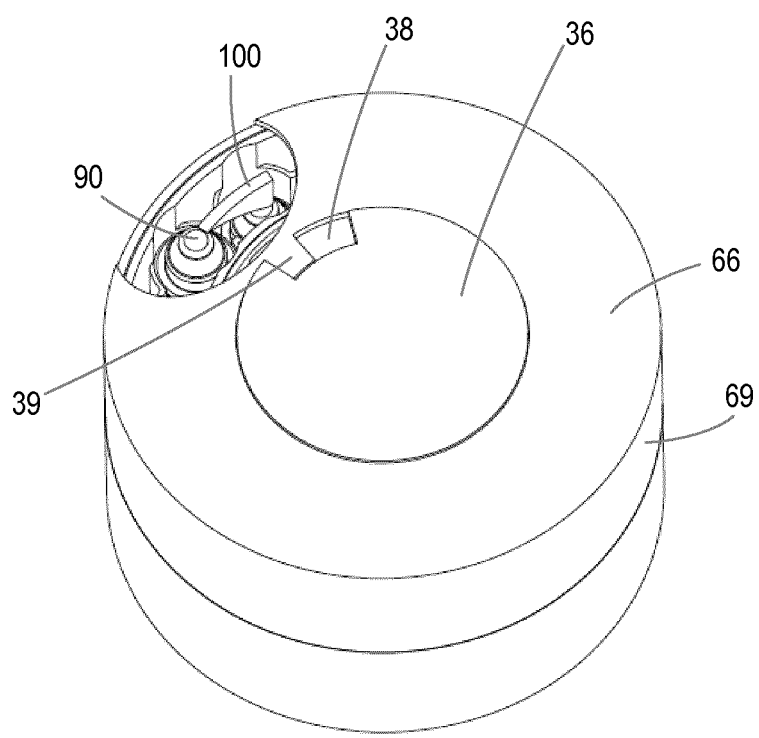
FIG. 11 is an assembled view of the control module and substance delivery module of FIG. 10.

According to one embodiment of the present invention, illustrated in FIGS. 10 and 11, a single actuator in the form of a cam 100 may be mounted on an internal surface of the cartridge lid 56, and brought into engagement with each vial 90 as it is desired to dispense the contents of the vial. According to this embodiment, the control module 6 comprises a substantially cylindrical main body 34 and a hub 36, protruding from a planar face of the main body 34. The hub 36 is also substantially cylindrical and includes a guide recess 38 formed on an outer planar face, which recess is dimensioned to cooperate with a guide lip 39 formed on the lid 56 of the cartridge 52. The hub 36 also comprises guide shoulders 42, 44 defining an opening 40 within which the locking ribs 80 of the indexing arms 78 formed on the cartridge base 54 may be received. The opening 40 also allows an electromechanical lock housed within the control module 6 to engage with the locking ribs 80 of the indexing arms 78, displacing the locking ribs and allowing for indexing of the cartridge base 54 with respect to the control module 6 and mouthpiece 8. As discussed above, a recess 32 is formed in the main body 34 of the control module, extending from the face opposite to that from which the hub 36 protrudes. The recess 32 is dimensioned to accept the housing 28 of the mouthpiece 8. The recess 32 communicates with a delivery passage 46 which extends through the main body 34 of the control module to open onto the face from which the hub 36 extends. The delivery passage 46 is radially aligned with the opening 40 for the electromechanical lock.

The control module 6 may also comprise an opening 50 through which a pressure sensor (not shown) may protrude. When assembled with the mouthpiece 8, the opening 50 communicates with the opening 30 on the mouthpiece 8 to allow a pressure sensor mounted within the control unit 6 to protrude into the inhalation flow path 26. The cooperating openings can be seen in the assembled sectional view of FIG. 4.

According to the embodiment of FIGS. 10 and 11, the cartridge lid 56 may comprise a top plate 66, and inner and outer annular skirts 67, 69. The cam 100 may be mounted on an inner surface of the top plate 66. On assembly of the substance delivery module 4, the lid 56 may be placed over the cartridge base 54 such that the cam 100 occupies the vacant position V on the cartridge base 54. A releasable coupling mechanism may couple the lid 56 to the cartridge base 54 for rotational motion in a first direction, and decouple the base 54 and lid 56 for rotational motion in a second direction.

In use, the substance control module 4 of the first embodiment is first assembled with the required drug or drugs sealed in the vials 90 and the vials 90 loaded in position adjacent their corresponding pistons 76. The cartridge lid 56 is placed over the cartridge base 54 and the substance delivery module 4 is then mounted on the control module with the vacant position V and cam 100 opposite the delivery passage 46. The mouthpiece 8 is also mounted on the control module 6, with the housing 28 received in the recess 32 and the aerosol generator 10 opposite the delivery passage 46. When it is desired to dispense a dose of the substance contained in the nebulizer 2, the nebulizer 2 is powered on. Rotation of the cartridge base 54 and lid 56 in the first direction brings a new piston 76 and vial 90 into a dispensing position in which the delivery opening 108 of the piston 76 is aligned with the delivery passage 46 of the control module and hence with the aerosol generator 10. Subsequent rotation of the cartridge lid 56 in the second direction brings the cam 100, mounted on an internal surface of the lid top plate 66 of the lid 56, into engagement with the vial 90 in the dispensing position, forcing the vial 90 onto its cooperating piston 76 as discussed above and dispensing the dose of substance. When delivery of the next dose is required, the above rotation steps are repeated, bringing the next vial/piston combination into the dispensing position and forcing the vial onto the piston to dispense the substance.

Indexing of the cartridge base 54 with respect to the control module 6 in order to bring a new vial/piston combination into the dispensing position may be controlled by the solenoid switch housed within the control module 6. On powering on the nebulizer 2, the solenoid switch may be activated, causing a part of the switch to enter the opening 40 and engage the locking rib 80 received in the opening 40. The solenoid switch displaces the locking rib 80 form the opening, allowing rotation of the cartridge base 56 in the first direction to bring a new vial/piston combination into a dispensing position. Each vial/piston combination may be brought into the dispensing position and then dispensed by subsequent rotation of the cartridge lid and/or base in the first and second directions until all vials in the substance delivery module have been dispensed. The cooperating recess 38 and guide lip 39 may act to prevent excess relative rotation between the cartridge lid 56 and the control module 6.

Figure 12:
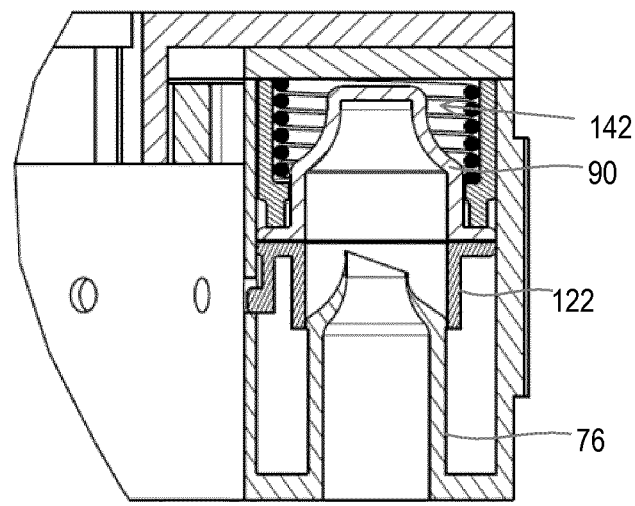
FIG. 12 is a partial sectional view of a substance container, piston and actuator.
Figure 13:
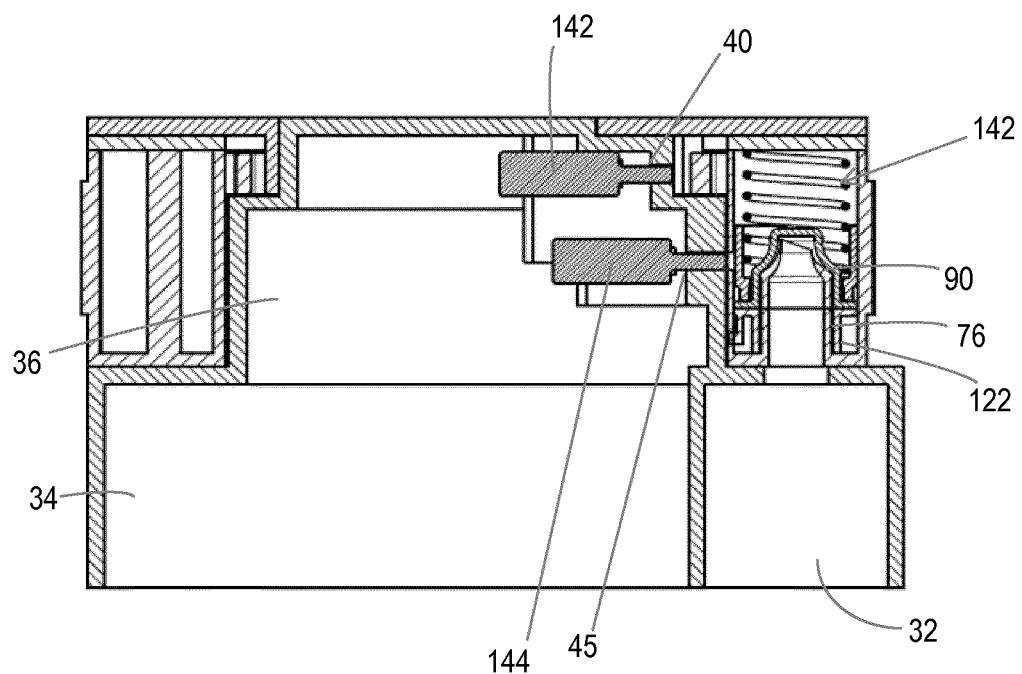
FIG. 13 is a sectional view of the components of FIG. 12 mounted on a control module and in a discharged position.

With reference to FIGS. 12 and 13, and in accordance with another embodiment of the present invention, the substance delivery module 4 may comprise a plurality of actuators, a dedicated actuator being mounted for cooperation with each vial. In this manner, each actuator may be activated to cause dispensing of the substance contained in its corresponding vial when the vial and its dedicated piston are in the dispensing position aligned with the delivery passage 46 and aerosol generator 10. As illustrated in FIGS. 12 and 13, each actuator may take the form of a compression spring 142 mounted around its corresponding vial 90. According to the embodiment of FIGS. 12 and 13, the cartridge lid 56 may comprise only a top plate 66 and inner skirt 67, and relative rotation between the lid 56 and cartridge base 54 may be permitted in both directions. Indexing of the cartridge base to bring a new piston/vial combination into a dispensing position may take place substantially as described above with respect to the example of FIGS. 10 and 11, with rotation of the cartridge base 54 effected by a user applying rotational force directly to the cartridge base.

According to the example of FIGS. 12 and 13, a releasable locking element 122 may retain each compression spring and may be released to allow the compression spring to force the vial onto its dedicated piston, so dispending the substance contained in the vial. The releasable locking element 122 may be released by a second solenoid switch housed within the control module. The second solenoid switch may engage the releasable locking element via a dedicated opening 45 in the control module, as illustrated for example in FIG. 13. FIG. 13 illustrates the first and second solenoid switches 142, 144 following dispensing of a vial 90 in the dispensing position.

In other examples (not shown) the substance delivery module 4 and control module 6 may be realised to support linear translation between the cartridge base of the substance delivery module and the control module, such that subsequent vials may be dispensed.

Embodiments of the present invention thus provide a substance delivery module and apparatus for delivery of a substance that are efficient and easy to use. The substance delivery module provides controlled dosing, with individual vials of substance each containing a single dose. Complete delivery of the dose is assured through the arrangement of the components forming the feed system. The feed flow path from vial through piston to aerosol generator is comparatively short, reducing to a minimum the surfaces that are wetted by the substance in passing, and so reducing substance wastage. In addition, by forcing the vial completely onto the piston, and dimensioning the piston to displace substantially the entire internal volume of the vial, maximum transfer of substance from the vial is assured. The delivery passage of the piston may be dimensioned to create a pressure gradient that further assists transfer of the substance from vial to piston and on to the aerosol generator. Embodiments of the invention thus reduce substance wastage and provide accurate substance dosing.

The shortened feed flow path also has advantages in the ease of use of the substance delivery module and apparatus. By reducing the surfaces wetted by the substance during delivery, the surfaces requiring regular cleaning are also reduced to a minimum. These surfaces are essentially found in the mouthpiece 8, meaning those surfaces requiring cleaning are found in a single component which may be removed and cleaned as required.

The dedicated delivery pistons help to ensure a greatly reduced risk of contamination. For each vial, a corresponding delivery piston essentially forms the feed flow path for that vial, delivering the substance contained in the vial to the aerosol generator 10. Each new vial thus benefits from an unused feed flow path, meaning that different substances can be loaded in different vials and dispensed through the same apparatus. For example, a treatment course comprising different medicaments for morning and afternoon dispensing may be contained in a single substance delivery module, with the substance vials loaded in alternating pattern in the cartridge. Risk of contamination between the substances is minimised by the design of the delivery module and apparatus. A cleaning substance, for example a volatile cleaning solution such as ethanol may be included in one or more of the vials spaced around the apparatus. This may represent a cleaning position, dispensing of the vial by a patient allowing for cleaning of the substance flow path. The apparatus may be locked during this time to prevent a patient inhaling the cleaning substance.

Separating the wetted and contaminated surfaces between the three units of the apparatus also assists in maximising the usage life of the individual units. The substance delivery module may be rendered entirely disposable, a new module provided with each new course of treatment. The mouthpiece may be cleaned between uses and between treatment courses and may thus have a longer usage life for example of between one and 24 months. The control module which has minimal contact with the inhalation flow and feed paths may benefit from a longer usage life of several years, and with appropriate cleaning may be used by several different patients.

Patient involvement with the substance to be dispensed is also minimised. The substance delivery module can be provided to a patient ready loaded with sealed vials and for example completely sterilized after assembly and before delivery to the patient. The patient is merely required to load the substance delivery module onto the control module and dispense the substance as described above.

It should be noted that the above-mentioned embodiments illustrate rather than limit the invention, and alternative embodiments may be envisaged without departing from the scope of the appended claims. The word "comprising" does not exclude the presence of elements or steps other than those listed in a claim, and the indefinite article "a" or "an" does not exclude a plurality. A single processor or other unit may fulfil the functions of several units recited in the claims. The mere fact that certain measures are recited in mutually different dependent claims does not indicate that a combination of these measured cannot be used to advantage. Any reference signs in the claims shall not be construed so as to limit their scope.

The invention claimed is:

1. A substance delivery module comprising:
   a plurality of substance containers;
   a plurality of pistons, wherein each substance container is mounted in the module for cooperation with a dedicated piston; and
   a plurality of actuators, each actuator mounted around a dedicated substance container, wherein each actuator is configured to engage its dedicated substance container and to urge the entire dedicated substance container onto its dedicated piston,
   wherein each substance container includes a cup and a sealing membrane; and
   wherein each actuator encircles the dedicated substance container.

2. A module as claimed in claim 1, wherein the substance containers are moveably mounted within the module, each substance container being mounted for motion onto its dedicated piston.

3. A module as claimed in claim 1, wherein the pistons and substance container are cooperatively shaped and dimensioned such that the pistons displace an internal volume of the substance containers.

4. A module as claimed in claim 1, wherein each piston having a cooperating substance container comprises a passage extending through the piston.

5. A module as claimed in claim 1, wherein the pistons comprise a cutting element, mounted on a leading surface of the pistons.

6. A module as claimed in claim 1, wherein each substance container has an internal surface and wherein each piston has an external surface cooperatively shaped to the internal surface such that the piston substantially occupies the entire internal volume of the substance container for which each piston is dedicated when the substance container is urged onto the piston.

7. A module as claimed in claim 1, wherein each cup comprises an annular lip to which the membrane is sealed.

8. A module as claimed in claim 7, wherein each actuator engages the annular lip of the dedicated substance container.

9. An apparatus for delivering a substance in aerosol form, comprising:
   an aerosol generator;
   an aerosol delivery conduit in fluid communication with the aerosol generator; and
   a substance delivery module comprising:
      a plurality of substance containers;
      a plurality of pistons, wherein each substance container is mounted in the module for cooperation with a dedicated piston; and a plurality of actuators, each actuator mounted around a dedicated substance container, wherein each actuator is configured to engage its dedicated substance container and to urge the entire substance container onto its dedicated piston, wherein each substance container includes a cup and a sealing membrane; and wherein each actuator encircles the dedicated substance container.

10. An apparatus as claimed in claim 9, wherein at least part of the apparatus comprises an anti-microbial surface.

11. An apparatus as claimed in claim 9, wherein each cup comprises an annular lip to which the membrane is sealed.

12. An apparatus as claimed in claim 11, wherein each actuator engages the annular lip of the dedicated substance container.

\* \* \* \* \*